United States Patent
Pischel et al.

(10) Patent No.: US 6,307,080 B1
(45) Date of Patent: Oct. 23, 2001

(54) WATER-SOLUBLE ZINC PYRUVATES OR THEIR HYDRATES, METHOD FOR THE PRODUCT ION THEREOF AND THEIR USE

(75) Inventors: Ivo Pischel, Trostberg; Henrich Hasko Paradies, Iserlohn, both of (DE)

(73) Assignee: SKW Trostberg Aktiengesellschaft, Trostberg (DE)

( * ) Notice: Subject to any disclaimer, the term of this patent is extended or adjusted under 35 U.S.C. 154(b) by 0 days.

(21) Appl. No.: 09/700,381

(22) PCT Filed: Jul. 8, 1999

(86) PCT No.: PCT/EP99/04812

§ 371 Date: Dec. 13, 2000

§ 102(e) Date: Dec. 13, 2000

(87) PCT Pub. No.: WO00/02841

PCT Pub. Date: Jan. 20, 2000

(30) Foreign Application Priority Data

Jul. 9, 1998 (DE) .............................. 198 30 770

(51) Int. Cl.⁷ ........................... C07F 3/06; A61K 31/315
(52) U.S. Cl. .............................. 556/131; 514/494
(58) Field of Search .............................. 556/131; 514/494

(56) References Cited

U.S. PATENT DOCUMENTS 5,980,477 * 11/1999 Kelly ...................................... 602/77

FOREIGN PATENT DOCUMENTS 92 15292    9/1992   (WO) .

OTHER PUBLICATIONS

G. Weitzel A1 A1: Hoppe–Seylers Z. Physiol. Chem., 292, pp. 286–302 (1953).

J. J. Berzelius: Annalan Der Physik Und Chemie, (36) 9 p. 1–29 (1835).

G. Fischer et al: J. Org. Chem. (53) 1, 214–216 (1988).

www.earnestjohn.com/products.htm. Mar. 2, 1999.

* cited by examiner

*Primary Examiner*—Porfirio Nazario-Gonzalez
(74) *Attorney, Agent, or Firm*—Fulbright & Jaworski, LLP

(57) ABSTRACT

Water-soluble zinc pyruvates and hydrates thereof of the formula I

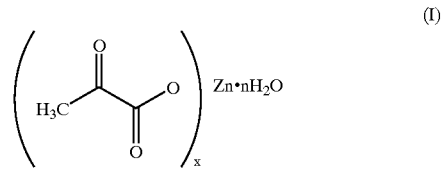

where x=1.8 to 2.2 and n=0 to 5 are described. The inventive zinc pyruvates are distinguished by a high purity and excellent storage stability and thermal stability and can be employed especially for use as therapeutic agent for treating diabetes, cold prophylaxis, virus inhibition, cytoprotection, as microbicide and as radical absorber and as food supplement or supplement for the prophylaxis and prevention of zinc deficiency symptoms.

19 Claims, No Drawings

WATER-SOLUBLE ZINC PYRUVATES OR THEIR HYDRATES, METHOD FOR THE PRODUCT ION THEREOF AND THEIR USE

The present invention relates to water-soluble zinc pyruvates and hydrates thereof having a high purity and good storage stability and thermal stability, a process for their preparation and use thereof.

It is known that salts of pyruvic acid, called pyruvates, have valuable physiological, therapeutic and dietary properties. Pyruvates are used to increase stamina and strength in the sports sector, for weight reduction and body fat reduction and as a protective substance for body cells and body tissue, particularly cardiovascular, hepatic, nephrotic, peritoneal and neuronal tissue, and as antioxidant, both as a substance for inhibiting radical formation and also as a radical absorber substance in body cells, body tissues and cells of the synovial tissue, in the health sector and as food supplement agent. In addition, pyruvates are used as wound healing preparations, for treating diabetes because of their action in reducing blood sugar and for treating kidney diseases(acute kidney failure, kidney stones suffering).

Furthermore, it has been known for over 100 years that zinc is an essential trace element for plants, animals and humans. The occurrence of a zinc deficiency in humans has been thought to be improbable for a long time. Therefore, the interest of dietetics in this trace element was initially low. In the 1950s, it was then demonstrated that zinc deficiency can occur in humans with typical symptoms. The research was intensified worldwide as in 1961 the endemic occurrence of hypogonadism and dwarfism in Iran and the Nile delta of Egypt could be refered to a zinc deficiency. Routine analytical measurements in foods and tissue samples contributed to a better understanding of the role of the trace element zinc in biochemical processes. Currently, the clinical symptoms of a severe zinc deficiency are known, but the pathological changes occurring in the zinc deficiency cannot be explained till now.

Zinc is a constituent of metalloenzymes and stabilizes organic structures and membranes. Over 200 different zinc-dependent enzymes have now been identified. Superoxide dismutase, alkaline phosphatase, DNA polymerase and RNA polymerase and carboxypeptidase are examples of these. Zinc participates in nucleic acid synthesis, protein metabolism, lipid metabolism, carbohydrate metabolism, bone metabolism, oxygen transport, dark adaptation and the antioxidative protective system of the human body. Zinc is essential for all forms of life because it plays an important role in transcription and translation and expression of genes. Some enzymes contain zinc in the active center, where it acts as electron acceptor. In other enzymes and non-enzyme proteins and in nucleic acids zinc has structural and stabilizing functions (zinc finger). In the pancreas zinc participates in insulin synthesis and insulin storage. In addition, it fulfills important tasks in the immune system.

In the case of zinc, in addition to the absolute content, the bioavailability is also critical for the importance of a food as a zinc source. Absorption of zinc from foods of animal origin is generally higher than from foods of plant origin. Zinc, which forms poorly absorbable complexes with phytic acid, has low availability from phytate-rich foods (for example whole kernel corn). Simultaneously increased consumption of the metals iron, copper, tin and cadmium also inhibit absorption. The presence of amino acids, peptides and organic acids increases bioavailability. Muscle meat, milk products, fish and particularly shellfish (for example oysters up to 160 mg of Zn/100 g) are good zinc sources. Dark meat (beef: 4.3 mg of Zn/100 g) has a higher zinc content than light meat (chicken: 1.0 mg of Zn/100 g). Most fruit and vegetables make only a small contribution to the zinc supply. The zinc content of cereal products is greatly dependent on the degree of processing, since zinc is predominantly localized in the outer layers of the grain. The mean absorption rate of zinc from different types of bread is around 10%, whereas this can be up to 40% from meat from various types of poultry.

Zinc is partly released from the bound form in foods by digestive enzymes and gastric acid, and binds loosely to low-molecular-weight ligands such as amino acids, peptides, organic acids and phosphates, which is of importance for the extent of zinc absorption. Zinc is absorbed by a saturable carrier process in the duodenum and jejunum. Absorbed zinc in blood plasma is bound to albumins, $a_2$-macroglobulin and transferrin and transported. The proportion of zinc bound to plasma proteins however makes up only approximately 20% of the zinc content in the blood. The greatest proportion (75%) is present as constituent of carboanhydratase in the erythrocytes. A further 3% is present as constituent of alkaline phosphatase in leukocytes.

Zinc is present in all body tissues and body liquids in differing concentrations. Body levels in adults are in total 2–3 g of zinc. Approximately 60% is present in skeletal musculature and 30% in the bones. Zinc is primarily an intracellular ion which occurs at only relatively low concentrations in extracellular fluids. Only 0.1% of the total body zinc circulates in the plasma. There zinc contents are subject to strict homeostatic control. Humans have to have a regular zinc uptake from food. Zinc is predominantly excreted via the intestine. It is lost here together with digestive secretions and sloughed intestinal epithelial cells. Endogenous losses can be 2 to 4 mg/day. A further 0.5 mg each are excreted with the urine and via the skin (skin scales, hair and sweat). In inflammatory intestinal and kidney diseases, and also in the case of alcoholism, excretion is significantly increased.

Severe forms of zinc deficiency have been observed in humans having congenital disturbances of zinc metabolism (acrodermatitis enteropathica), in patients having inadequate parenteral nutrition and in patients with Morbus-Crohn's disease. The clinical pattern of symptoms includes dermatitis at the ends of limbs and around the mouth, diarrhea, loss of appetite, hair loss and neuropsychiatric disturbances, thrieving depression and growth depression, increased susceptibility to infections and delayed wound healing and disturbances of sexual development.

Furthermore, zinc can be used to prevent the progressive impairment of glucose tolerance with age. With increasing age, independently of body weight, there is a highly significant impairment in glucose tolerance and a significant decrease in insulin secretion after administration of glucose. The basal serum insulin values decrease with increasing age. A reduction in glucose conversion rates with age has been found for glucose metabolism of the brain. Animal experiments and clinical studies indicate that zinc deficiency plays an integrating role in the progressive impairment of age-related glucose tolerance.

Zinc is particularly suitable for treating diabetes mellitus. Zinc improves glucose tolerance and can markedly increase insulin action. Zinc is an important therapeutic for diabetics. According to the German Diabetes Society (Deutsche Diabetes-Gesellschaft, DDG), there currently live in Germany approximately 4 million diabetics (5% type I diabetics, 95% type II diabetics).

According to estimates of leading diabetologists, this figure will double by the year 2000.

Hyperglycemia characterizes diabetes mellitus as a cardinal symptom. In diabetics there is either an insulin deficiency and/or an insulin resistance. Insulin regulates the blood glucose level. Trace elements cannot cure diabetics or act as therapies alone. Despite this, the essential trace element zinc plays a critical role in regulation of blood sugar. With zinc deficiency pathological glucose tolerance frequently occurs, which can be normalized alone by regular zinc administration.

The essential trace element zinc improves the insulin storage in type II diabetics. Zinc deficiency inhibits insulin activity and insulin receptor formation. The daily zinc requirement, according to the German Nutrition Society (Deutsche Gesellschaft für Ernährung, DGE), in adults is from 12 to 15 milligrams. The average zinc intake via foods (particularly in oysters, innards, meat) is somewhat below this recommendation. Diabetics belong to zinc supply risk groups, since their zinc losses via urine are markedly increased. The level of zinc excretion increases with the extent of glucosuria (sugar excretion via urine). This relates especially to diabetics suffering from diabetic nephropathy. The McNair study shows urine zinc excretions higher by 50 to 150% in diabetics compared with healthy persons. If urine sugar values are positive, the zinc loss is much higher and can exceed 2 to 3 times the norm. In type II diabetics, Perger and coworkers, after administration of zinc for 6 weeks, found a decrease in the average fasting blood sugar values from 250 to 142 mg %. In other studies, both the fasting and also postprandial blood sugar level decreases markedly with zinc administration. Therefore the daily intake of from 15 to 30 milligrams of zinc via tablets appears useful.

With zinc administration, wounds heal better, for example in the case of what is termed diabetic foot on the base of poor blood sugar values, peripheral occlusive disease and diabetic polyneuropathy. This is due, inter alia, to the antiinflammatory effect of zinc.

The exact human zinc requirement is unknown. According to balance studies, the daily obligatory zinc losses which must be replaced are 2.5 mg. At an average bioavailability of 20%, this gives for Germany a recommended daily intake of 15 mg for men. Because of the lower average bodyweight, a zinc intake for women of 12 mg/day is recommended. In the USA the recommended daily intake (RDI) for adults is 15 mg of zinc.

In the literature, zinc pyruvate has only been described to date once by J. J. Berzelius, Annalen der Physik und Chemie (1835) 36, 20, as a zinc oxide salt of pyruvic acid. Beilstein, Volume 3 of the main series, page 612, cites this reference, specifying zinc pyruvate as trihydrate.

Berzelius produced the salt either by transforming basic zinc carbonate or metallic zinc with dilute pyruvic acid. The resultant salt, according to Berzelius, is a sparingly soluble powder. However, following Berzelius's instructions for synthesizing zinc pyruvate gives a sparingly soluble powder which, by modern analytical testing methods (NMR, IR, HPLC), has been unambiguously identified as zinc parapyruvate.

It has also been found that the previously known process for producing so-called "zinc pyruvates" by neutralizing pyruvic acid with zinc carbonate, zinc hydroxide or zinc oxide and the reaction of zinc metal with pyruvic acid leads to a sparingly soluble zinc parapyruvate with large amounts of byproducts, since pyruvic acid and the pyruvate ions react via aldol addition reactions or aldol condensation reactions to acyclic or cyclic dimers and polymer s of pyruvic acid, respectively.

Zinc parapyruvates contaminated in this way are unsuitable for use as therapeutics and furthermore are not sufficiently storage-stable, because during storage, inter alia, dimeric, polymeric and cyclic compounds a re formed, which can be toxic.

Acyclic compounds which may be mentioned are parapyruvic acid (4-hydroxy-4-methyl-2-oxoglutaric acid) and its salts, and the higher aldol addition products. In addition, oxalic acid and methylsuccinic acid can be formed as byproducts. The acyclic pyruvic acid polymers can form via lactonization reactions, ketalization reactions and other reactions cyclic compounds, for example 2-hydroxy-2-methyl-4-oxoglutaric acid -5-lactone, trimesic acid derivatives, isophthalic acid derivatives and pyrantricarboxylic acid derivatives (reference: Beilstein, Basic Series Volume 3, pp. 608–613; 1st Supplementary Series, pp. 217–219; 2nd Supplementary Series, pp. 393–401; 3rd Supplementary Series, pp. 1146–1156; 4th Supplementary Series, pp. 1505–1510). These byproducts occur in the same manner in the storage of zinc pyruvates which are prepared by the previously known process. These abovementioned acyclic and cyclic byproducts and decomposition products of pyruvic acid and its salts can be physiologically incompatible or toxic.

The object therefore underlying the present invention was to develop water-soluble and storage-stable zinc pyruvates which do not have the mentioned disadvantages corresponding to the prior art, but have a high purity and are therefore physiologically safe.

This object was achieved according to the invention by preparing the zinc pyruvates and hydrates thereof of the formula I

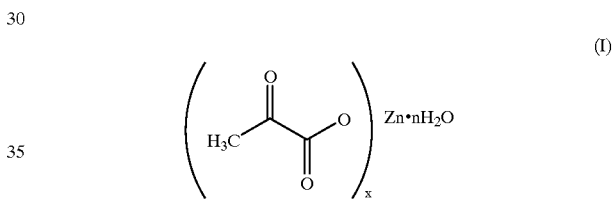

where x=1.8 to 2.2 and n=0 to 5.

This is because it has surprisingly been found that the inventive zinc pyruvates have a high purity and are virtually free of any toxic byproducts and have an excellent storage stability and thermal stability.

This was surprising, because in the inventive preparation, pyruvic acid does not undergo, or undergoes to a very limited extent, condensation reactions and decomposition reactions with formation of aldol adducts, although transition metals such as zinc should catalyze the polymerization of pyruvic acid.

The inventive zinc pyruvates which have high water solubility and can be unambiguously characterized by elemental analysis, IR spectroscopy, NMR spectroscopy and by HPLC content determination, contain the zinc cation and the pyruvate anion, which can be present as oxopropionate and/or 2,2-dihydroxypropionate anion, in a molar ratio of from 1.8 to 2.2:1 and preferably in the stoichiometric ratio of 2:1.

In addition, the inventive zinc pyruvates are present either completely anhydrous or in the form of hydrates, where n can be from 0 to 5 and preferably from 0 to 3. According to a preferred embodiment, the zinc pyruvates are present in a solid microcrystalline form which is distinguished by a particularly high storage stability.

The zinc pyruvate content can thus be from 72.7 to 100% and the crystal water content from 0 to 27.3% (equivalent to from 0 to 5 mol of crystal water). Based on the anhydrous substance, the zinc pyruvate content is from 99 to 100%.

The inventive zinc pyruvates are prepared by reacting zinc salts of organic acids or acidic organic keto compounds or hydroxyl compounds with pyruvic acid in the temperature range from −20 to +90° C., in the presence or absence of a solvent or diluent. Preferably, the reaction is carried out at from 10 to 50° C.

The organic acid used can in principle be any physiologically safe carboxylic acid which may optionally be substituted with amino, keto or hydroxyl groups. Preferably, the organic acid or acidic organic keto compound or hydroxyl compound used is an acid selected from the group consisting of formic acid, acetic acid, propionic acid, butyric acid, lactic acid, ascorbic acid, citric acid, tartaric acid, succinic acid, maleic acid, fumaric acid, malic acid, aspartic acid, benzoic acid, gluconic acid, isovaleric acid, oleic acid, glycine or lysine.

These zinc salts of the organic acids or acidic organic keto compounds or hydroxyl compounds can be used in anhydrous form, as hydrates or as moist products.

The pyruvic acid can also be used in the inventively proposed process optionally as free acid, as aqueous solution or dissolved in a solvent or diluent. Suitable solvents or diluents in this case are preferably water and/or organic solvents, for example alcohols (methanol, ethanol, isopropanol, cyclohexanol), ethers (diethyl ether, tetrahydrofuran, 1,4-dioxane), ketones (acetone, methyl ethyl ketone, cyclohexanone), esters (methyl acetate, ethyl acetate, ethyl formate), organic acids (formic, acetic, propionic, lactic, pyruvic acid) and aliphatic hydrocarbons (pentane, hexane, cyclohexane) and aromatic hydrocarbons (toluene).

However, the organic zinc salts can also be reacted with pyruvic acid as such in the absence of solvent or diluent.

According to a preferred embodiment, it is also possible in the context of the present invention to generate pyruvic acid as an intermediate, that is to say, for example, by reacting alkali metal pyruvate, for example sodium pyruvate or potassium pyruvate, with an inorganic acid, for example sulfuric acid or hydrochloric acid, in the temperature range from −20 to +90° C., preferably from −10 to +60° C.

The ratio of organic zinc salt to pyruvic acid can be varied within broad limits, but it has proved to be particularly advantageous to react the organic zinc salts and pyruvic acid in stoichiometric (2:1) or approximately stoichiometric ratios (1.8 to 2.2:1).

The procedure of the inventive process is substantially unproblematic, and it can be performed by customary methods and in known processing apparatuses such as in kneaders, mixers, blade dryers and stirred vessels. In this manner zinc pyruvates are obtained without further workup steps in high yield and purity.

The inventive zinc pyruvates have valuable biological and medical properties and are used as therapeutics for treating diabetes, cold prophylaxis, virus inhibition, cytoprotection, as microbicide and as free-radical scavenger or as food supplement or as supplement for the prophylaxis and prevention of zinc deficiency syndrome, such as growth disorders in children and adolescents, weight loss, increased susceptibility to infections, poor wound healing, taste and odor disorders, delayed puberty, decrease of appetite, vision disorders, diarrhea, skin diseases, hair loss and emotional disorders.

The inventive zinc pyruvates surprisingly show antiviral properties, in particular against influenza A and influenza B viruses, herpes I, II and III viruses and the rhinoviruses, antimicrobiological activities against bacterial infections, for example Pseudomonas immunofluorescens, Pseudomonas aerogenes strains, staphylococci and streptococci and causative agents of sinusitis, tonsilitis and catarrhal inflammations both of virucidal or bacterial genesis, pyoderma and boils and refractory antiseptic wound treatments. The antimycotic activities relate in particular to dermatomycoses, mycoses of general types caused by yeasts, molds, dermatophytes, candidoses and yeasts and also pityriasis versiculor. This also relates to prophylaxis of the skin and mucosa, in particular in the case of postoperational surgical wound treatment in the case of (possibly occurring) bacterial wound infections and secondary infections in the dermatological area, where they are caused by Gram-positive and/or Gram-negative meclocyclin-sensitive microorganisms.

The inhibition of influenza A and B viruses by zinc pyruvates was demonstrated experimentally by inhibition of influenza A- and B-induced viral hemagglutination (vHA) of erythrocytes (RBC) and in vitro in cell cultures by the inhibition of viral infectivity. By comparing the determined inhibition constants of the virus-induced infectivity (plaque reduction, PFU=plaque forming units) in Madin-Daby-Canine-Kidney (MDCK) cells, the cytotoxicity of zinc pyruvate, and the vHA at the level of $IC_{50}$ concentrations, it was possible to demonstrate a) the potentiation of the antiviral action as exemplified by $IC_{50}$ or vHA and reduction of infectivity by zinc pyruvate; b) the cytoprotective action of zinc pyruvate at concentrations at which not only pyruvate but also zinc salts (inorganic and organic) demonstrate no biological activity, especially inhibitory activities, and c) the therapeutic index of zinc pyruvate (2000) which is high owing to its very low cytotoxicity, and a very high in vitro selectivity ratio for zinc pyruvate which exists neither for pyruvate nor for zinc salts (zinc ions). The same therapeutic index could not be achieved by administering the two components, such as $Zn^{2+}$ions and pyruvate, alone or as a loose combination, or in a sequential manner. In this case the therapeutic index even falls to 340, if, for example, first pyruvate and then $Zn^{2+}$ is added to the cell cultures, in the reverse case (first $Zn^{2+}$, then pyruvate) even to 250. Therefore, administering the inventive zinc pyruvate has a synergistic action which leads to significant advantages compared with administration in the form of the individual components zinc and pyruvate.

A further synergistic effect of zinc pyruvate is the reduction of active oxygen radicals and/or hydroxyl radicals, in particular in inflammatory processes. Thus, faulty lytic reactions in which both aggressive oxygen radicals and nitrogen oxide radicals participate, originating as pathogenic mechanisms in inflammatory diseases, are inhibited by zinc pyruvate. For example, inter alia, the cytotoxic action of the secondary products of these aggressive radicals is inhibited by zinc pyruvate and, inter alia, thus depolymerization of hyaluronic acid, proteoglycans, collagen fibrils, cytoskeletons and adhesin proteins and mucous and membranous tissue is also suppressed or a temporary cell protection is caused, as a result of which the infiltration of aggressive free radicals can be prevented.

Circulating monocytes which, in the absence of inflammatory stimulants, penetrate the tissue and thus become resident macrophages, after activation, for example by superoxides (hydroperoxides), NO and $O_2$ radicals and by inflammatory events, play a great role in the activation of enzymes, growth factors, cytokines and lymphokines. Lymphokines are reduced at inflammatory points in order to induce defense mechanisms against the invasion of bacterial or viral influences (LPS, hemagglutinin, neuraminidase, laminins, s-ICAM). Zinc pyruvate supports or triggers the stimulation of the host-defense function by secreting interferon-γ (IFN-γ) and thus plays a regulatory part in the secretory activity and humoral defense via the biosynthesis of IL-4 and IL-10. Especially the regulatory and in part inhibitory effect of zinc pyruvate on the release of $HO_2^{\cup}$ was demonstrated by the experimental measurement of respiratory burst activity quantitatively under the influence of zinc pyruvate.

Finally, the invention relates to a process for treating disorders selected from the group consisting of diabetes, colds, viral and microbial infections and zinc deficiency and to a process for scavenging radicals or for cytoprotection, in which an effective amount of an inventive zinc pyruvate is administered to the patient to be treated, which can be a human or an animal.

The zinc pyruvate is preferably administered orally. However, other forms of administration are conceivable, for example parenteral or topical adminstration. The amount of zinc pyruvate administered can, because of the low toxicity, be varied within broad ranges. The treatment duration depends on the type and severity of the disease to be treated. However, the inventive preparations can be administered without damage to health over a period of several weeks to months.

Administration is preferably performed in the form of a pharmaceutical composition which comprises as active compound a water-soluble zinc pyruvate, in particular a zinc pyruvate as defined above as active compound if appropriate together with pharmacologically safe excipients, diluents and aids. In addition, obviously, the composition can comprise other pharmaceutical active compounds which are used together with the zinc pyruvate to treat a disease. For example, daily doses of from 0.01 to 25 mg per kg of bodyweight of the treated patient are possible, which corresponds to supplying a total daily amount of from 0.7 to 1750 mg for a person weighing 70 kg.

The examples below are intended to illustrate the invention in more detail.

EXAMPLES

A. Preparation Examples

Example A.1

To a solution of 88 g (1 mol) of pure pyruvic acid (99% pure) in a mixture of 500 ml of ethyl acetate and 1000 ml of glacial acetic acid are added at 20° C. in the course of 30 minutes 105 g (0.48 mol) of zinc acetate dihydrate and the mixture is stirred for 3 hours. Finally, the zinc pyruvate is filtered off with suction and washed with 2×250 ml of ethyl acetate. The yield of zinc pyruvate monohydrate is 122 g (95% of theory).

$(C_3H_3O_3)_2Zn \cdot 1H_2O$, calculated: C 27.99%, H 3.13%, Zn 25.39%; found: C 28.09%, H 3.28%, Zn 25.44%; m.p.>300° C.; IR (KBr) [1/cm]: 644, 737, 854, 1190, 1350, 1372, 1412, 1650, 1703, 3222; $^1$H—NMR ($D_2O$, 300 MHz): δ=2.42 (s, 3H, $CH_3$—CO), 1.54 (s, 3H, $CH_3$—$C(OH)_2$); HPLC contents (zinc pyruvate): 92.8% =99.8% zinc pyruvate monohydrate.

Example A.2

To 455 g (5 mol) of 98.7% pure pyruvic acid are added at 40° C. in the course of 1 hour 55 g (0.25 mol) of zinc acetate dihydrate. The mixture is stirred at 40° C. for a further 3 hours. After cooling to 15° C., the mixture is stirred for 1 hour. Finally, the zinc pyruvate is filtered off with suction, washed with 2×100 ml of ethyl acetate and dried at 50° C. and 15 mbar. The yield of zinc pyruvate monohydrate is 61 g (95% of theory).

Example A.3

At a temperature of from 15 to 20° C., to a suspension of 110 g (1 mol) of sodium pyruvate in 200 ml of ethyl acetate 64.3 g (0.49 mol) of 70% strength sulfuric acid are added dropwise over a period of 45 minutes. After 3 hours the precipitated sodium sulfate is filtered off with suction and the residue washed with 2×40 ml of ethyl acetate. To the filtrate are added 250 g of concentrated acetic acid. The mixture is heated to 35° C. In the course of 30 minutes, 96.7 g (0.48 mol) of zinc acetate monohydrate are introduced. The suspension is stirred further for 3 hours. Finally, the zinc pyruvate is filtered off with suction and washed with 2×100 ml of ethyl acetate. The product is dried to constant weight at 50° C. in a vacuum drying cabinet. The yield of zinc pyruvate monohydrate is 124 g (96% of theory).

Example A.4

To a solution of 45.5 g (0.5 mol) of 98.7% pure pyruvic acid in 200 ml of glacial acetic acid and 200 g of ethyl acetate are added 20 g of water and 38.9 g (0.25 mol) of zinc formate are introduced at 40° C. in the course of 1 hour. The mixture is stirred for 3 hours at this temperature. After cooling to 15° C. the mixture is stirred for a further 1 hour. Finally, the zinc pyruvate is filtered off with suction, washed with 2×100 ml of ethyl acetate and dried at 50° C. and 15 mbar. The yield of zinc pyruvate trihydrate is 71.4 g (97% of theory)

$(C_3H_3O_3)_2Zn \cdot 3H_2O$, calculated: C 24.55%, H 4.12%, Zn 22.27%; found: C 24.64%, H 4.18%, Zn 22.52%; m.p.>300° C.; IR (KBr) [1/cm]: 644, 737, 854, 1190, 1350, 1372, 1412, 1650, 1703, 3222; $^1$H—NMR ($D_2O$, 300 MHz): δ=2.42 (s, 3H, $CH_3$—CO), 1.54 (s, 3H, $CH_3$—$C(OH)_2$); HPLC contents (zinc pyruvate): 81.5% =99.8% zinc pyruvate trihydrate.

Example A.5 (Comparison)

Repetition of the instructions for preparing the zinc oxide salt of pyruvic acid of J. J. Berzelius, Annalen der Physik und Chemie (1835) 36, 20.

In 105.6 g (0.6 mol) of 50% strength aqueous pyruvic acid are dissolved 34.2 g (0.1 mol) of zinc hydroxide carbonate hydrate (Aldrich 36, 720-6). After the end of carbon dioxide evolution, the mixture is stirred for a further 2 hours. Finally, the resultant white precipitate is filtered off with suction, washed with 50 ml of water and 50 ml of methanol and dried at 50° C. and 15 mbar. The analyses clearly characterized the precipitate as zinc parapyruvate. The yield of zinc parapyruvate trihydrate is 79.1 g (80% of theory).

$(C_6H_6O_6)Zn \cdot 3H_2O$, calculated: C 24.55S, H 4.12%, Zn 22.27%; found: C 24.64%, H 4.18%, Zn 22.52%; m.p.>300° C.; IR (KBr) [1/cm]: 642, 669, 798, 1075, 1113, 1140, 1205, 1228, 1342, 1396, 1474, 1609, 1677, 1713, 3408; $^1$H-NMR ($D_6$—DMSO, 300 MHz): δ=1.27 (s, 3H, $CH_3$—CO), 2.99 (d, 1H, $CH_2$), 3.25 (d, 1H, $CH_2$); HPLC contents (zinc parapyruvate): 81.5% =99.8% zinc parapyruvate trihydrate.

Example A.6 (Comparison)

In 35.2 g (0.2 mol) of 50% strength aqueous pyruvic acid are dissolved 6.5 g (0.1 mol) of metallic zinc powder. After the completion of hydrogen evolution, the mixture is stirred for a further 2 hours. Finally, the resultant white precipitate is filtered off with suction, washed with 50 ml of water and 50 ml of methanol and dried at 50° C. and 15 mbar. The analyses clearly characterized the precipitate as zinc parapyruvate. The yield of zinc parapyruvate tetrahydrate is 24.0 g (77% of theory).

B. Use Examples

Example B.1

Assays for Macrophage Activation and Cytokines

A modified assay was carried out according to Barbior et al. (B. M. Barbior, R. S. Kipnes, J. T. Curnutte, J. Clin. Invest., 52, 741, 1973). In this assay $5 \times 10^5$ macrophages per titer and well were used in the presence of 10% fetal calf serum with increasing concentrations of zinc pyruvate ($0-0.1-1 \times 10^3$ mM). The introduced number of macrophage cells corresponds to the release of $HO_2^U$ being, or ensures that it is, exactly proportional to the concentration of the cell count. The blank value (blank, only buffer) and a negative control and a positive control (authentic substance, zinc pyruvate) were carried out such that specificity of the superoxide anions was ensured. Thus the wells were inoculated with 15 µg of superoxide dismutase at a cell count of $3.0 \times 10^5$ in order to act as a negative control.

The macrophages were activated either with phorbol myristic ester (20 µg/ml) or zymosan (100 µg/ml). The macrophages thus stimulated were pretreated as negative control, blank or with the appropriate concentration of zinc pyruvate (authentic compound) (determination of cytoprotection) or added directly to the assay (determination of inhibition), then washed with 0.02 M $NaH_2PO_4$ buffer (pH 6.5, 20° C.) and then incubated with 0.5 ml of reaction mixture/Hank's solution (phenol red-free), 80 µM of ferricytochrome C (Sigma type IV) and 5 mM $NaN_3$, which acts as a cytochrome oxidase inhibitor, and with stimulant (≈50–70 µl) at 37° C. for 20 min. Cytochrome C reduction was measured by the change in extinction at 550 nm. The superoxide anion concentration was determined via the difference in absorption at 550 nm in the presence or absence of superoxide dismutase using the experimentally determined (working) extinction coefficient of 18.95/mM/cm (reduced or oxidized). The biochemical activities of inhibition of oxygen free radical formation were measured and evaluated in accordance with Michaelis-Menten kinetics.

Inhibition of the release of superoxide radicals (anions) in the presence of zinc pyruvate gave an inhibition constant of $K_i=550\pm25$ mM at an association constant of zinc pyruvate to the macrophages under these in-vitro conditions of 150 nM. When the macrophages were pretreated with 1.0 mM zinc pyruvate for a period of 10 min at 37° C. and subsequently stimulated with phorbol myristic ester under the same assay conditions, inhibition constants of $K_{i(1)}=150\pm25$ mM and $K_{i(1)}=670\pm55$ mM were found, respectively. The two different inhibition constants are explained via the allosteric inhibition of the pretreated macrophages with respect to the release of $HO_2^U$ by already inhibited macrophages which are no longer available to the assay or have become refractory (allosteric inhibition). The binding constant additionally determined by equilibrium dialysis of only 150 nM zinc pyruvate to the macrophages at a cell count of $10^5$ also verifies the unusual allosteric course of inhibition in the presence of zinc pyruvate. Despite the increase in the concentration of the stimulant, although under saturated conditions (zinc pyruvate/macrophage), neither the binding constants for zinc pyruvate and that of the macrophages, nor the inhibition constants $K_i$ changed, but more oxygen radicals were inactivated per unit of time. This meant that in the presence of zinc pyruvate the turnover number of the macrophages to destroy the active and aggressive oxygen radicals increased from ≅350 to ≅7100.

Example B.2

Assay of Inhibition of NO Secretion

The assay of the effect of nitrogen oxide secretion by zinc pyruvate was performed using the GRIESS reaction (A. H. Ding, C. F. Nathan & D. J. Stuehr, J. Immunol., 141, 2407, 1988). The modified GRIESS reagent was composed as follows: 1 ml of 0.5% (g/g) naphthaleneethylenediamine·$H_3PO_4$, 1 ml of 0.5% (g/g) sulfanilacidamide in 1% (g/g) $H_3PO_4$. In order to activate the NO burst for macrophages, the macrophages (cell count: $2.0 \times 10^5$) were incubated for 2 hours at 37° C. in 500 µl of GRIESS reagent by adding 75 units/ml of IFN-γ. After addition of 20 µg/ml of lipopolysaccharide (LPS, E. coli, MRE 600), the NO determination was initiated and started, respectively. The mixture was incubated for 12 hours at 37° C. under a stream of $N_2$. As negative or positive control in the NO biosynthesis, 200 µg/ml of $N^6$-monoethylarginine were added together with LPS. The supernatant was separated off from the cells by centrifugation, GRIESS reagent was added to the appropriate volume and then the extinction was measured after 5 min at 525 nm (glass cuvette, 1 cm path length, 25° C.).

The inhibition constants for zinc pyruvate which were determined were $K_i=600\pm50$ mM, and with pretreatment of the macrophages with zinc pyruvate $K_i=230\pm60$ mM, although with only one Michaelis-Menten inhibition constant. That is to say, via the concentrationdependent inhibition of the active, aggressive and cytotoxic oxygen radicals and hydroperoxides (according to pH) and the cytosolic activation of the cells by zinc pyruvate, both the humoral and the cellular activation components including the MHC III complex on the macrophage mannosyl receptor are modulated. This modulation also includes IL-1, IL-6 and the TNF-α factors. These elements occupy especially the pro-inflammatory positions with corresponding reduction of the pro-inflammatory cytokine secretion by zinc pyruvate. In this case, although the macrophages, in the presence of zinc pyruvate, and in contrast to IFN-γ, IL-10, IL-4 and IL-13, are in the activated state, this is in such a manner that they can stimulate the necessary protective cytokines, such as IL-1, IL-6 and TNF-α and can thus ensure protection from LPS, bacterial products (fever, edema, release of prostaglandins and possibly leukotrienes, SLS products) and also from viral products (increase in autoimmune activities). Thus the zinc pyruvate, via cellular induction, makes a contribution toward reducing the inflammatory events, by stimulating the antagonists of the pro-inflammatory cytokines.

Example B.3

In-vitro Inhibition of Viral Hemagglutination (vHAI) and Infectivity by Reducing Plaques in the Presence of Zinc Pyruvate As mentioned above, the antiviral properties of zinc pyruvates were tested on epithelial MDCK cells for the influenza strains A/Chile/1/83/or influenza B/Singapore/27/79/. The assay conditions corresponded to those of K. Tabita, A. Sugiura, C. Enomoto, M. Furuyama, Med. Microbiol. Immunol., 165, 9–14, 1975. The infected MDCK cells were treated for 30 min with zinc pyruvate and compared with cell cultures which had not been infected with influenza virus. A qualitative and quantitative control of the advancing infection was additionally performed by determining the viral proteins and the count of infectious particles in the cell culture supernatant.

The cell cytotoxicity was determined correspondingly under identical culture conditions with identical but uninfected MDCK cells. The validity of the results obtained was determined on the basis of the 95% confidence limit using the t-test values for the corresponding confidence ranges.

The inhibition of influenza-induced hemagglutination (vHAI) of erythrocytes (RBC) was carried out in accordance with the protocol of G. N. Rogers, T. Pritchett, J. L. Lane, J. C. Paulsen, Virology, 131, 394–408, 1983. The results are summarized in Table 1.

The low cytotoxicity of zinc pyruvate is notable and surprising. The lysis of RBC cells begins at 1000 µg/ml, that is considerably higher than for the inhibitory constants determined in vHAI, which are of the order of magnitude of 50 µg/ml. The $LD_{50}$ concentration for the MDCK cells is on average from 800 to 1000 µg/ml for zinc pyruvate. That is to say all of the values found are far above those of the biochemically active inhibitor concentrations, so that the therapeutic concentrations of zinc pyruvate in no manner exert a cytotoxic effect on the cells in vitro, and for which reason the measured inhibition of the individual parameters is due to a specific interaction with the cellular apparatus or the virus and not to the lysis of the MDCK cells.

TABLE 1

Hemagglutination inhibition (HAI), plaque reduction assay of Zn pyruvate

| No. | Inhibitor | HAI, µm $IC_{50}$ | Potency HAI | Plaque µM | Reduction[a] % |
|---|---|---|---|---|---|
| 1 | $Zn(Ac)_2$ | 150.0 | 6.0 | 1700 | 15 |
| 2 | $Zn(Py)_2$ | 25.3 | 19.9 | 90.5 | 67 |
| 3 | $ZnCl_2$ | 100.0 | 5.0 | 1200 | 20 |
| 4 | $ZnO.H_2O$ | ≈200.0 | 4.5 | 1700 | 15 |

[a]The values are the percentage reduction in number of plaque per unit volume (well) which are caused by viral lysis of the infected cells.

What is claimed is:

1. A water-soluble zinc pyruvate of Formula I

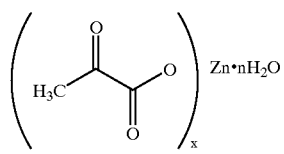

(I)

where x is from 1.8 to 2.2 and n is from 0 to 5.

2. The zinc pyruvate according to claim 1, wherein x is 2 and n is from 0 to 3.

3. The zinc pyruvate according to claim 1, wherein the pyruvate anion is 2,2-dihydroxypropionate.

4. The zinc pyruvate according to claim 1 in solid microcrystalline form.

5. A process for preparing zinc pyruvate according to claim 1 comprising reacting a zinc salt of an organic acid or acidic organic keto compound or hydroxy compound with pyruvic acid at a temperature ranging from −20 to +90° C., optionally in the presence of a solvent or diluent.

6. The process according to claim 5, wherein the temperature is from 10 to 50° C.

7. The process according to claim 5, wherein the organic acid is selected from the group consisting of an amino-, keto- and hydroxy-carboxylic acids.

8. The process according to claim 5, wherein said zinc salt comprises an organic acid or acidic organic keto compound or hydroxyl compound selected from the group consisting of formic acid, acetic acid, propionic acid, butyric acid, lactic acid, ascorbic acid, citric acid, tartaric acid, succinic acid, maleic acid, fumaric acid, malic acid, aspartic acid, benzoic acid, glycolic acid, isovaleric acid, oleic acid, glycine and lysine.

9. The process according to claim 5, wherein said zinc salt of the organic acid or acidic organic keto compound or hydroxyl compound are anhydrous, hydrated or a moist product.

10. The process according to claim 5, wherein the pyruvic acid is anhydrous, in an aqueous solution, or dissolved in a solvent or diluent.

11. The process according to claim 5, wherein the solvent or diluent used is an organic solvent or water.

12. The process according to claim 11, wherein the organic solvent is selected from the group consisting of alcohols, ethers, ketones, esters, organic acids, aliphatic hydrocarbons and aromatic hydrocarbons.

13. The process of claim 5, wherein the pyruvic acid is formed as an intermediate by reacting alkali pyruvate with an inorganic acid at temperature of from −10 to +60° C.

14. A pharmaceutical composition comprising the water-soluble zinc pyruvate of claim 1 and at least one of a pharmaceutically acceptable carrier, diluent and adjuvant.

15. A method of treating diabetes or treating colds inhibiting virus, enhancing cytoprotection, inducing micobicidal activity and absorbing radicals comprising administering an effective amount of the zinc pyruvate of claim 1 to a subject in need thereof.

16. A method for the prophylaxis or prevention of symptoms associated with zinc deficiency comprising administering an effective amount of the zinc pyruvate of claim 1 to a subject in need thereof.

17. A process for treating a condition selected from the group consisting of diabetes, colds, viral infections, microbial infections and zinc deficiency comprising administering effective amount of a composition according to claim 14 to a subject in need thereof.

18. A process for scavenging radicals comp mging administering to a subject an effective amount of a composition according to claim 14 to a subject.

19. A process for inducing cytoprotection comprising administering to a subject an effective amount of a composition according to claim 14 to a subject.

* * * * *